US 6,686,317 B2

(12) United States Patent
Netherland et al.

(10) Patent No.: US 6,686,317 B2
(45) Date of Patent: Feb. 3, 2004

(54) SUPPORTED FLURIDONE COMPOSITIONS AND METHODS

(75) Inventors: Michael D. Netherland, Carmel, IN (US); Steve D. Cockreham, Indianapolis, IN (US)

(73) Assignee: SePro Corporation, Carmel, IN (US)

( * ) Notice: Subject to any disclaimer, the term of this patent is extended or adjusted under 35 U.S.C. 154(b) by 0 days.

(21) Appl. No.: 10/045,444

(22) Filed: Oct. 22, 2001

(65) Prior Publication Data

US 2003/0045429 A1 Mar. 6, 2003

Related U.S. Application Data

(60) Provisional application No. 60/313,836, filed on Aug. 21, 2001.

(51) Int. Cl.[7] .......................... A01N 25/08; A01N 43/40
(52) U.S. Cl. .......................... 504/155; 504/367
(58) Field of Search .................. 504/155, 367

(56) References Cited

U.S. PATENT DOCUMENTS

| | | | |
|---|---|---|---|
| 4,116,665 A | 9/1978 | Krumkalns | |
| 4,235,619 A | * 11/1980 | Taylor | .......... 71/66 |
| 5,125,954 A | 6/1992 | Powell et al. | |
| 5,830,827 A | 11/1998 | Maeda | |
| 5,945,114 A | 8/1999 | Ogawa et al. | |
| 5,981,440 A | 11/1999 | Bratz et al. | |
| 6,001,382 A | 12/1999 | Levy | |
| 6,030,924 A | 2/2000 | Mayer et al. | |

FOREIGN PATENT DOCUMENTS

| WO | WO 98/12921 | 4/1998 |
|---|---|---|
| WO | WO 99/51091 | 10/1999 |

OTHER PUBLICATIONS

Fluridone (Sonar®) Fact Sheet (Mar. 2000), Washington State Dept. of Health.
Material Safety Data Sheet, Sonar SRP Herbicide (Effective Date Oct. 20, 2001).
Specimen Label, Sonar SRP, SePRO Corporation (2002).

* cited by examiner

Primary Examiner—S. Mark Clardy
(74) Attorney, Agent, or Firm—Woodard, Emhardt, Moriarty, McNett & Henry LLP

(57) ABSTRACT

Described are preferred solid formulations of fluridone having advantageous fluridone release profiles. Preferred formulations comprise carriers including attapulgite and/or bentonite clay. Also described are methods of using and manufacturing such compositions.

30 Claims, 2 Drawing Sheets

SUPPORTED FLURIDONE COMPOSITIONS AND METHODS

REFERENCE TO RELATED APPLICATIONS

This application claims the benefit of U.S. Patent Application Serial No. 60/313,836 filed Aug. 21, 2001, which is hereby incorporated by reference in its entirety.

BACKGROUND

The present invention relates generally to the control of aquatic plants, and in particular to supported fluridone compositions useful for the control of aquatic plants.

The compound 1-methyl-3-phenyl-5-3-(trifluoromethyl)-phenyl-4(1H)-pyridinone, commonly known as fluridone, has proven to be a highly effective aquatic herbicide for controlling a wide range of undesirable aquatic plants. To date, fluridone has been commercially available in both liquid and solid (pellet) formulations. Commercial pellet-form fluridone compositions have utilized a carrier comprised of kaolin clay, which has provided a slow release of fluridone over an extended period of time. This has facilitated the maintenance of low levels of fluridone in treated water bodies for extended periods of time.

The use of aquatic herbicides such as fluridone has become a common method for controlling invasive aquatic weeds. However, the use of such herbicidal control presents risks and difficulties including the potential impact on the local environment, variations in conditions of treatment caused by water flow and other factors, and the potential for differential herbicide-tolerance to develop. For these reasons, it is important that any fluridone formulation used provides an optimal treatment regimen.

In light of this background, there is a need for improved fluridone compositions useful for the control of aquatic plants. Such compositions will desirably facilitate the ability to maintain lethal threshold concentrations of fluridone so as to avoid situations in which insufficient levels of fluridone are present thus resulting in treatment failure as well as increasing the chances of the plant becoming more tolerant. The present invention addresses these needs.

SUMMARY OF THE INVENTION

It has been discovered that advantageous fluridone compositions can be prepared having a relatively quick initial release of fluridone while also maintaining an advantageous extended fluridone release. Such compositions can be prepared, for example, by supporting fluridone on a solid carrier comprising a suitable hormite mineralogy such as an attapulgite type mineralogy, or on a solid carrier comprising a suitable bentonite mineralogy or another substantially swellable clay mineralogy exhibiting similar release characteristics. The fluridone can be loaded on the carrier, for example, to provide a composition comprised about 1% to about 20% by weight fluridone. Preferred fluridone compositions are solid, formed articles such as pellets, tablets or granules, and are effective to release at least 20% of their fluridone load within about 10 days after immersion in static, distilled water. Still further preferences exist where the composition is comprised about 1% to about 10% by weight of fluridone, more preferably about 3% to 7% by weight fluridone. The solid carrier is desirably at least 20% by weight comprised of attapulgite type mineralogy.

In another embodiment, the present invention provides a method of controlling aquatic plants which comprises introducing into a body of water containing the plants an effective amount of a fluridone composition of the invention.

In still another embodiment, the present invention provides a method for manufacturing a fluridone composition which comprises supporting fluridone on a solid carrier containing attapulgite type mineralogy.

The present invention provides fluridone compositions having advantageous fluridone release profiles and which are effective for the control of aquatic plants. The invention also provides methods of making and using such compositions. These and additional embodiments, as well as advantages and features of the invention will be apparent from the descriptions herein.

DESCRIPTION OF THE PREFERRED EMBODIMENTS

Figure 1:
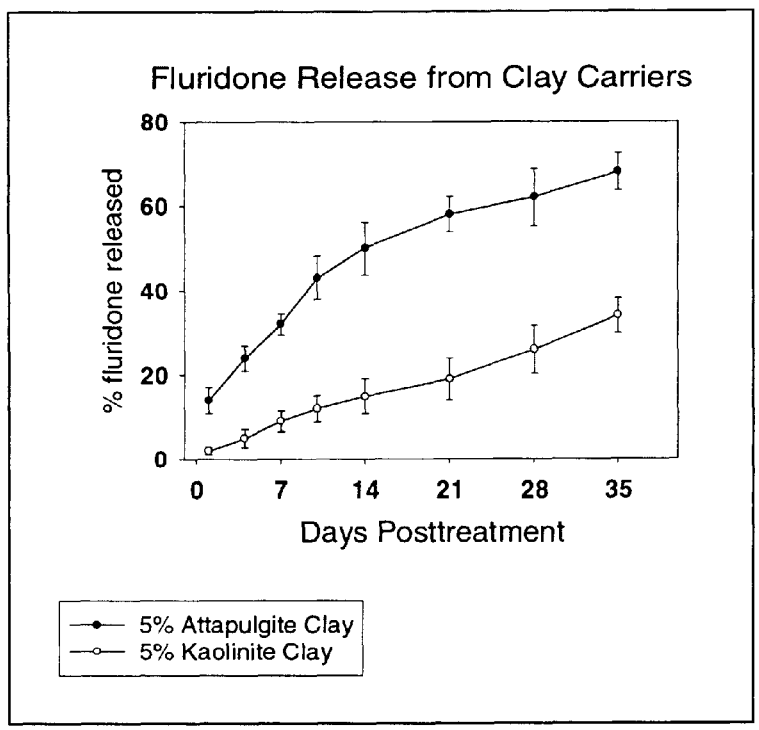
FIG. 1 depicts a graph of % fluridone released over time for an inventive attapulgite-supported fluridone composition and a kaolinite-supported fluridone composition.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, in one preferred embodiment, the present invention provides solid herbicidal formulations useful for the control of aquatic plants, wherein the formulations include fluridone loaded upon a solid support comprising attapulgite or bentonite mineralogy. The present invention also provides methods for controlling aquatic plants which comprise introducing into a body of water having the plants an effective amount of such formulations of the invention. Still further, the present invention provides methods for manufacturing herbicidal compositions which comprise the step of providing a solid carrier comprised of attapulgite or bentonite, and loading the carrier with an effective amount of fluridone.

The chemical fluridone, formally named 1-methyl-3-phenyl-5-3-(trifluoromethyl)phenyl-4(1H)-pyridinone, is a known herbicide for use in the control of aquatic weeds. Fluridone is sold under the trade name SONAR®, available from SePRO Corporation, Carmel, Indiana.

Fluridone is a systemic herbicide that is absorbed from water by plant shoots and from hydrosoil by roots. It inhibits carotenoid synthesis which in turn enhances the degradation of chlorophyll. This produces a characteristic bleached appearance to susceptible plants. Fluridone is useful in the complete or partial control of many noxious plants. For example, fluridone is useful in the complete control of the floating plant common duckweed (*Lemna minor*), of the emersed plants spatterdock (*Nuphar luteum*) and water-lily (*Nymphaea* spp.), of the submersed plants bladderwart (Utricularia spp.), common coontail (*Ceratophyllum demersum*), common elodea (*Elodea canadensis*), Brazilian elodea (*Egeria densa*) fanwort (*Cabomba caroliniana*), hydrilla (*Hydrilla verticillata*), naiad (Najas spp.), pondweed (Potamogeton spp.) other than Illinois pondweed, and watermilfoil (Myriophyllum spp.) other than variable leaf watermilfoil), and of the shoreline grass paragrass (*Urochloa mutica*). Fluridone is useful in the partial control of the floating plants common watermeal (*Wolffia columbiana*) and salvinia (Salvinia spp.), the emersed plants alligatorweed (*Alternanthera philoxeroides*), American lotus (*Nelumbo lutea*), cattail (Typha spp.), creeping waterprimrose (*Ludwigia peploides*), parrotfeather (*Myriophyllum aquaticum*), smartweed (Polygonaum spp.), spikerush (Eleocharis spp.), waterpurslane (*Ludwigia palustris*), and watershield (*Brasenia schreberi*), of the submersed plants Illinois pondweed (*Potamogeton illinoensis*), limnophila (*Limnophila sessiliflora*), tapegrass or American eelgrass (*Vallisneria americana*), and variable leaf watermilfoil (*Myriophyllum heterophyllum*), and the shoreline grasses barnyardgrass (*Echinochloa crusgalli*), giant cutgrass (*Zizaniopsis miliacea*), reed canarygrass (*Philaris arundinaceae*), southern watergrass (*Hydrochloa caroliniensis*) and torpedograss (*Panicum repens*). There are significant inter-species variations in susceptibility to fluridone, with some species usually susceptible to concentrations as low as about 5 ppb, and others usually susceptible to only higher concentrations such as 150 ppb.

The present invention provides in one aspect a solid herbicidal composition comprising fluridone and a carrier containing attapulgite (also known as palygorskite) mineralogy or another similar hormite clay having channels defined by octahedral and tetrahedral units of the clay mineral structure. In this regard, attapulgite (or palygorskite) is a known clay mineral that can be found, for example, in Georgia, Florida and France. Attapulgite is also known as "Fullers Earth". The structure of the attapulgite mineral shows silica chains similar to those in amphibole to be essential components of its structure. The chemical formula for attapulgite (palygorskite) can be represented as $(Mg,Al)_5 (Si,Al)_8O_{20}(OH)_2 \cdot 4H_2O$. As isolated and sold, attapulgite clays may contain other clay minerals, for example calcium montmorillonite. Still other clay minerals are typically present in relatively lower amounts, for example including kaolinite, quartz, feldspar and/or mica. Preferred attapulgite clays for use as starting materials in the invention are composed of attapulgite and calcium montmorillonite mineralogy, for example in a ratio of about 2:1 to about 1:2, respectively, more typically in a ratio of about 2:1 to about 1:1, respectively (e.g. as determinable using x-ray diffraction analysis).

The present invention provides in another aspect a solid herbicidal composition comprising fluridone and a carrier containing bentonite (i.e. sodium bentonite) or another substantially swellable clay exhibiting a similar beneficial fluridone release profile. As is known, the term bentonite was first applied to a particular, highly colloidal, plastic clay found near Fort Benton in the Cretaceous beds of Wyoming. It has the unique characteristic of swelling to several times its original volume when placed in water, and it forms thisxotropic gels with water even when the amount of bentonite in such gels is relatively small. Bentonite having sodium (Na+) as either the predominant or as an abundant exchangeable ion typically has very high swelling capacities and forms gel-like masses when added to water. Such compositions have also proven to provide a quick initial release of fluridone, combined with effective levels of extended release.

Consistent with the above discussions, in accordance with the invention, the attapulgus or bentonite type mineral can be used alone or potentially in combination with other minerals or solid materials, including for example montmorillonite, kaolinite, and other clays. These other clay mineralogies may occur in the isolated attapulgite- or bentonite-containing starting material, or may be separately obtained and blended therewith. Preferred compositions of the invention will have a clay carrier component at least about 20% by weight comprised of attapulgite or similar hormite mineralogy or of bentonite mineralogy, more preferably at least about 40%, and most preferably at least about 50% by weight. Clay carrier components essentially 100% comprised of attapulgite/hormite or bentonite mineralogy are also contemplated as being within the scope of the present invention. It has been discovered that the use of these materials as carriers for fluridone provides compositions having highly advantageous fluridone release properties. In preferred formulations, these properties include, for example, a relatively quick initial release of fluridone to provide minimum lethal levels at an early stage in the treatment regimen, combined with a sustained fluridone release to provide prolonged contact as necessary for successful control.

Compositions of the invention in the form of solid, formed granules or particles, such as pellets or tablets, will also typically include one or more binders. Suitable such binders include for instance lignin binders or starch binders suitable for application to aqueous environments. Usually, such binders are used as coatings for the pellets, tablets or other formed articles to improve their integrity. They may also be incorporated within the articles in addition to or as an alternative to coatings.

As to ratios, solid formulations of the invention will preferably be comprised about 1% to about 20% by weight of fluridone (based on solids), more preferably about 1% to about 10% by weight fluridone, and most preferably about 3% to about 7% by weight fluridone. These solid formulations will typically be comprised about 1 to 10% by weight of binder (based on solids), more typically in the range of about 1 to 5% by weight binder. The remainder of the compositions of the invention may be constituted by the carrier and any other conventional ingredients present.

More preferred compositions of the invention will be in the form of pellets. As known in the art, pellets can be prepared by forming an admixture of the carrier and the active (fluridone), and adding water to form an extrudable mixture. That slurry is then extruded, cut, coated with binder, and dried to provide pellets of an appropriate size which are three-dimensionally stable. In such processes, the final, dried pellets typically contain up to about 5% moisture. Preferred pellets will have diameters ranging from about 1/16 inch to about 1/4 inch, and lengths ranging from about 1/16 inch to about 1/2 inch for application in the aquatics fields.

As noted above, it has been discovered that solid formulations can be prepared which provide beneficial, quick and yet long-lasting fluridone release profiles. In particular, preferred solid formulations of the invention will release at least about 20% of their fluridone load within 10 days after immersion in static distilled water, more preferably at least about 30% of their fluridone load within that period. Further, particularly advantageous solid formulations of the invention will have the following release profile when immersed in static distilled water.

| Days after Immersion | % Fluridone Released |
| --- | --- |
| 1 Day | At least 10% |
| 7 Days | At least 20% |
| 14 Days | At least 40% |
| 28 Days | At least 50% |

Solid formulations having these advantageous release profiles will provide for improved control of aquatic plants in many aquatic sites. In this regard, known concentrations of solid formulations of the invention can be introduced into a body of water for treatment, and will rapidly provide a minimum effective level of fluridone for plant control, and thereafter maintain at least that level for extended periods of time.

Bodies of water to be treated with the inventive methods will typically be freshwater bodies such as ponds, lakes, wetlands, reservoirs, rivers or irrigation canals, although other bodies of water may also be treated. Fluridone is a slow-acting herbicide that must remain in contact with the plant for several weeks to achieve effective control of most aquatic weeds. Thus, in accordance with the preferred methods of the invention, the fluridone composition will be applied in amounts sufficient to maintain the desired level in the body of water under treatment for at least about 4 weeks, and typically in the range of about 6 to about 16 weeks or more. For typical applications, the fluridone levels to be maintained will be in the range of about 1 parts-per-billion (ppb) to about 150 ppb more typically in the range of about 5 ppb to about 50 ppb in the body of water under treatment.

For the purpose of promoting a further understanding of the present invention and its features and advantages, the following specific examples are provided. It will be understood that these examples are illustrative and not limiting in nature.

EXAMPLE 1

Fluridone Release in Water

Two pellet formulations were prepared containing 5% fluridone. One formulation included attapulgite clay as the carrier, and the other included kaolinite clay as the carrier. The pellet diameter in each formulation was 1/16 inch. Samples of each formulation were weighed to provide a target fluridone concentration for the test system. Each formulation was then placed in a known volume of water in a 1 Liter Erlenmeyer flask. The pellets remained undisturbed at the bottom of the containers and water samples were collected at various times to determine the percent of fluridone released into the water column. The experimental systems were not exposed to any ultraviolet light, thus preventing the loss of any fluridone from the test system. Samples were then taken at 1, 3, 7, 10, 14, 21, 28 and 35 days, and used to calculate the percentage of the original fluridone load released. At the end of the sampling period, the remaining water and formulation were vigorously agitated to force the release of any fluridone that remained on the pellet. The water was then assayed again to insure that measured and theoretical concentrations agreed. The results are set forth in FIG. 1. As the results demonstrate, the formulation including the attapulgite carrier exhibited surprisingly rapid release of the fluridone as compared to the formulation including the kaolinite carrier. At the same time, the attapulgite formulation provided a sustained release of fluridone as necessary for successful plant control using this agent.

EXAMPLE 2

Fluridone Release in Water/Sediment System

Figure 2:
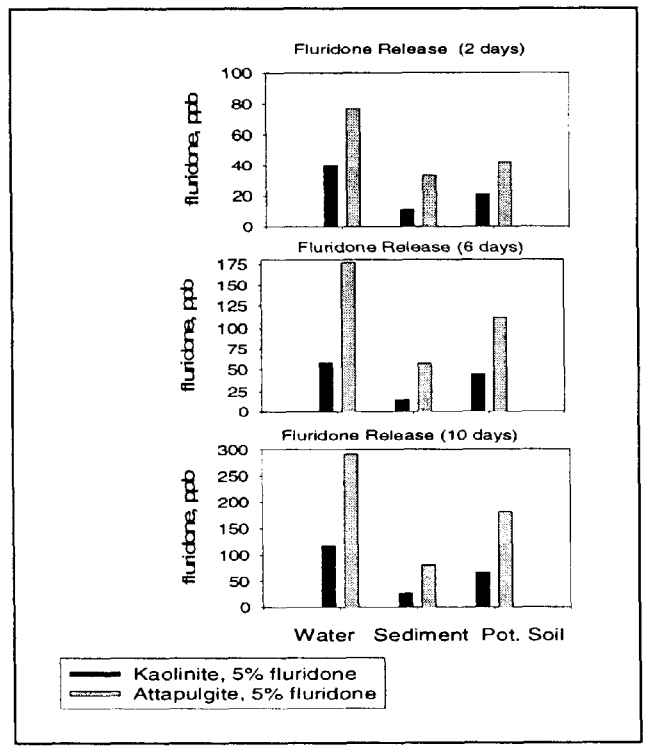
FIG. 2 depicts bar graphs showing fluridone concentrations released from an inventive attapulgite-supported fluridone composition and a kaolinite-supported fluridone composition after 2, 6 and 10 days in each of water alone, water+sediment, and water plus a standard potting soil.

Studies were conducted to determine the role that sediments play in release from attapulgite-based and kaolinite-based fluridone formulations identified in Example 1. One organic sediment (10% organic) collected from a local lake and a standard potting soil (2% organic) were weighed and each was placed in the bottom of a 50 L container. The sediments were approximately 2 inches in depth. In addition, one set of replicate tanks received a 2-inch layer of sand (0% organic). An exact volume of water was added and then a known amount of the test formulation was added to the system. The pellets remained undisturbed on the sediments and water samples were collected at various times to determine the percent of fluridone released into the water column. The experimental systems were not exposed to any ultraviolet light, thus preventing the loss of any fluridone from the test system. The results are shown in FIG. 2. The results demonstrate that the addition of sediment does impact the rate of fluridone release from the test formulations; nonetheless, the attapulgite-based formulation still provides a much quicker fluridone release.

EXAMPLE 3

Field Experiment Using Attapulgite Clay Formulation

The attapulgite type clay formulation identified in Example 1 (5% fluridone) was applied to Lake Wales, Fla. (252 acres) at a target concentration of 42 ppb. Residues were monitored at 1, 2, 3, 4, 6, 13, 20, 28, 35, 40, and 54 days posttreatment to evaluate release performance under field conditions. A typical treatment with Sonar™ SRP treatment (a commercially available 5% fluridone/kaolinite clay formulation) would achieve a maximum concentration of approximately 15 to 30% of the theoretical application rate at 20 to 40 days posttreatment. Therefore maximum expected residues would be in the range of 6.3 to 12.6 ppb for the Sonar™ SRP product. The attapulgite formulation provided significantly different release profile, achieving an average concentration of 15 ppb at 20 days posttreatment and 22 ppb at 40 days posttreatment.

EXAMPLE 4

Figure 3:
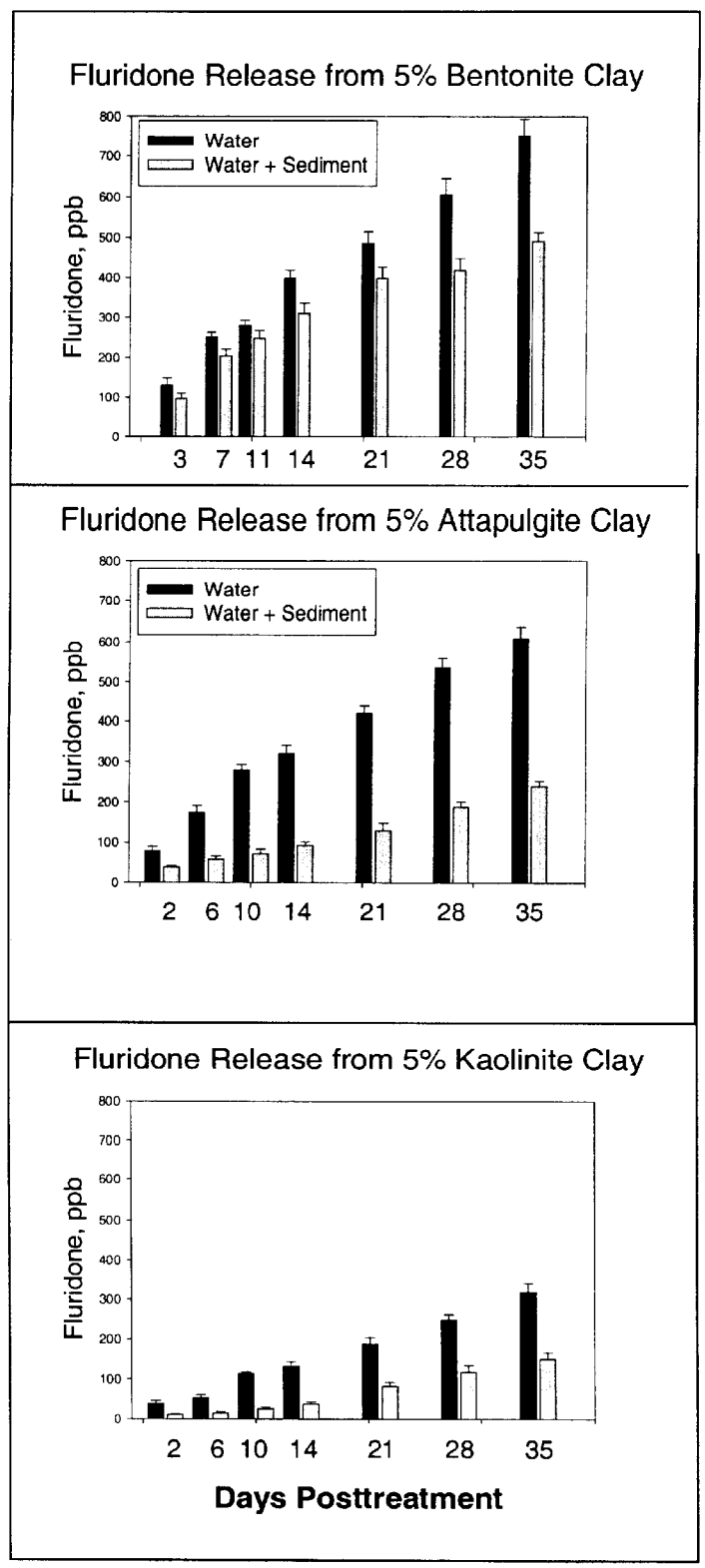
FIG. 3 depicts bar graphs showing fluridone concentrations released over time from inventive attapulgite-supported and bentonite-supported fluridone compositions in each of water alone and a water+sediment system.

Fluridone Release from Attapulgite, Bentonite and Kaolinite Carriers in Water and Water+Sediment Systems The procedures of Example 2 with regard to water and water+sediment (10%) systems were repeated using similar pellet formulations of fluridone loaded on bentonite, attapulgite and kaolinite to a level of 5%. The systems were established to release a theoretical total of 1000 ppb of fluridone to the systems. The results are shown in FIG. 3. The bentonite and attapulgite formulations released fluridone much more quickly, while maintaining a steady release over an extended period of time. The bentonite formulation performed particularly well in the water+sediment system, maintaining a large percentage of its release capacity exhibited in the corresponding water (only) system.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A herbicidal composition, comprising fluridone loaded on a solid carrier comprising aggregate particles containing attapulgite or bentonite.

2. The herbicidal composition of claim 1, wherein the composition is comprised of about 1% to about 20% by weight of fluridone.

3. The herbicidal composition of claim 2, wherein the composition is comprised about 1% to about 10% by weight of fluridone.

4. The herbicidal composition of claim 3, wherein the composition is comprised about 3% to about 7% by weight of fluridone.

5. The herbicidal composition of claim 1, which is effective to release at least about 20% of the loaded fluridone within seven days after immersion in static water.

6. The herbicidal composition of claim 5, which exhibits the following release profile when immersed in static water:

| Days after Immersion | % Fluridone Released |
| --- | --- |
| 1 Day | At least 10% |
| 7 Days | At least 20% |
| 14 Days | At least 40% |
| 28 Days | At least 50%. |

7. The herbicidal composition of claim 1, wherein the carrier is comprised at least about 20% by weight of attapulgite or bentonite.

8. The herbicidal composition of claim 1, wherein the carrier is comprised at least about 50% by weight of attapulgite or bentonite.

9. The herbicidal composition of claim 1, wherein the composition is comprised about 1% to about 10% by weight of binder.

10. The herbicidal composition of claim 9, wherein the composition is comprised about 1% to about 5% by weight of binder.

11. The herbicidal composition of claim 10, wherein the composition is in the form of pellets or tablets.

12. The herbicidal composition of claim 11, wherein the composition is in the form of pellets.

13. The herbicidal composition of claim 12, wherein the composition includes a lignin binder.

14. A method for controlling aquatic plants which comprises introducing into a body of water a herbicidal formulation comprising fluridone loaded on a solid carrier comprising aggregate particles containing attapulgite or bentonite.

15. The method of claim 14, wherein the herbicidal formulation is comprised about 1% to about 20% by weight of fluridone.

16. The method of claim 15, wherein the herbicidal formulation is comprised about 1% to about 10% by weight of fluridone.

17. The method of claim 16, wherein the herbicidal formulation is comprised about 3% to about 7% by weight of fluridone.

18. The method of claim 14, wherein the carrier is at least about 70% by weight comprised of attapulgite.

19. The method of claim 18, wherein the herbicidal formulation is in pellet form.

20. A method of manufacturing a herbicidal composition, comprising loading fluridone on a solid carrier comprising aggregate particles containing attapulgite or bentonite.

21. The method of claim 20, wherein the fluridone is loaded to a level of about 1% to about 20% by weight of the herbicidal composition.

22. The method of claim 21, wherein the fluridone is loaded to a level of about 1% to about 10% by weight of the herbicidal composition.

23. The method of claim 20, wherein the herbicidal composition is in pellet form, and the method comprises:

preparing an extrudable slurry comprising the fluridone and the carrier;

extruding the slurry to form an extrusion;

cutting the extrusion to form pellets; and coating the pellets with at least one binder; and drying the pellets.

24. A quick release fluridone herbicidal composition, comprising fluridone loaded on a solid carrier comprising aggregate particles, wherein said composition is effective to release at least about 20% of the loaded fluridone within seven days after immersion in static water.

25. The herbicidal composition of claim 24, which exhibits the following release profile when immersed in static water:

| Days after Immersion | % Fluridone Released |
| --- | --- |
| 1 Day | At least 10% |
| 7 Days | At least 20% |
| 14 Days | At least 40% |
| 28 Days | At least 50%. |

26. The herbicidal composition of claim 24, wherein the carrier contains hormite clay mineralogy.

27. The herbicidal composition of claim 26, wherein the carrier contains attapulgite mineralogy.

28. The herbicidal composition of claim 27, wherein the carrier is at least about 20% comprised of attapulgite mineralogy.

29. The herbicidal composition of claim 24, wherein the carrier contains bentonite clay minerology.

30. The herbicidal composition of claim 24, wherein the solid carrier is in pellet form or tablet form.

* * * * *